United States Patent [19]

Miyauchi et al.

[11] Patent Number: 5,700,251
[45] Date of Patent: Dec. 23, 1997

[54] EPIDURAL CATHETER

[75] Inventors: Hidekazu Miyauchi, Kusatsu; Katsuhiro Hiejima, Ootsu, both of Japan

[73] Assignee: Nissho Corporation, Osaka, Japan

[21] Appl. No.: 567,390

[22] Filed: Dec. 1, 1995

[30] Foreign Application Priority Data

Dec. 2, 1994 [JP] Japan .................... 6-299420

[51] Int. Cl.$^6$ .................................. A61M 5/00
[52] U.S. Cl. ............... 604/264; 604/44; 604/167; 604/283; 604/272
[58] Field of Search ............... 604/264, 44, 272, 604/280, 283, 167

[56] References Cited

U.S. PATENT DOCUMENTS

| | | | |
|---|---|---|---|
| 4,808,157 | 2/1989 | Coombs | 604/44 |
| 4,863,439 | 9/1989 | Senderson | 604/264 |
| 4,958,901 | 9/1990 | Coombs | 604/44 |
| 5,085,645 | 2/1992 | Purdy et al. | 604/167 |
| 5,156,596 | 10/1992 | Balbierz et al. | 604/264 X |
| 5,207,648 | 5/1993 | Gross | 604/264 X |
| 5,250,038 | 10/1993 | Melker et al. | 604/264 |

*Primary Examiner*—Michael Powell Buiz
*Assistant Examiner*—N. Kent Gring
*Attorney, Agent, or Firm*—Kubovcik & Kubovcik

[57] ABSTRACT

A catheter body includes a main lumen and an auxiliary lumen. The main lumen has an outlet opening located at a distal end of the body and an inlet opening at a proximal end. The auxiliary lumen has an outlet opening located behind and spaced from the distal end a distance of 5–10 cm and an inlet lateral opening located toward the proximal end. An adapter for providing inlet ports communicating with the inlet openings of the main lumen and auxiliary lumen is provided on the catheter body. The adapter includes three members detachably connected to one another. The forward and middle members have threaded portions which engage one another and the middle and rearward members also have threaded portions which engage with one another. Annular seals are provided between the forward and middle members and the middle and rearward members. The adapter can be readily attached to the catheter body and an external device for dosing a liquid medicine can be attached to the adapter.

13 Claims, 7 Drawing Sheets

EPIDURAL CATHETER

BACKGROUND OF THE INVENTION

1. Field of the Invention

The present invention relates to a catheter and, more particularly, to an epidural catheter adapted for use in long-term epidural anesthesia.

2. Prior Art

Many patients including, for example, postoperative patients and terminal cancer patients suffer from incessant pain. Recently, pain clinics have been established for the treatment and control of such pain.

Sustained long-term epidural anesthesia is one of the treatment methods which many pain clinics have recently adopted. In epidural anesthesia, a catheter which remains in an epidural space is continuously dosed with a narcotic through the catheter. Since narcotic acceptors are spread from end to end along the backbone, the narcotic for local anesthesia or hyposensitivity can act directly on any desired acceptor, without requiring other acceptors to be blocked.

The catheter is caused to "dwell" in the epidural space by first inserting the curved distal piercing end of a tubular metallic needle through the patient's skin and into his or her epidural space. After confirming that the piercing end is positioned correctly, a stylet is withdrawn from the tubular needle so that a desired length of the catheter is introduced therethrough. Then, the tubular needle is slowly removed from the patient, with the catheter being subsequently secured to his or her back by means of a suitable adhesive. Finally, an injector or a long-term dosing apparatus is connected to the proximal end of the catheter so that a narcotic can be supplied to the patient.

It is noted that in epidural anesthesia the piercing needle has to be removed after the catheter is inserted. If the needle is left in the patient, then it is likely that the catheter will be damaged or that tissue surrounding the needle will be injured. Thus, any device for feeding a narcotic that has a diameter larger than that of the catheter should not be connected to the proximal end of the catheter before removal of the piercing needle. Practitioners conducting medical operations have first removed the needles and then attached a suitable adapter to the proximal end of each catheter, before connecting a suitable device to each adapter and dosing a narcotic.

A typical example of a currently available catheter for long-term epidural anesthesia is made and sold by B. Braun A. G. under the trade name "PERIFIX." This catheter has a single lumen and a single orifice situated in the distal end of the catheter. The diameter of this orifice for delivery of a narcotic is substantially the same as the diameter of the lumen. When dosing a narcotic, the piercing end of the needle is removed after the catheter is inserted and before an injector or other dosing apparatus is attached to the proximal end of the catheter through a connector.

In the use of catheters having a single outlet orifice, practitioners must feel for epidural spaces in which a prescribed narcotic is to be introduced. As a consequence, practitioners often have erroneously introduced catheters into intervertebral spaces and caused local anesthesia of undesired vertebral nerves. In such instances, the practitioners have had to repeat the insertion procedure including the piercing of the patient's back, thereby increasing the potential for injuries and prolonging the operation.

The catheter mentioned above usually has at its distal end only one output orifice for the delivery of liquid medicine. Thus, only a narrow restricted region around the distal end of the catheter could be anesthetized. In a case in which anesthesia of a wider region is necessary, a larger amount of narcotic should be dosed to the patient.

In order to resolve this problem, a catheter of the double-tube type was proposed in Japanese Utility Model Publication No. 58-13859. As shown in FIG. 7 of the present application, outlet openings 300 and 400 for delivery of liquid medicine communicate with respective flow paths formed independently of each other. This catheter makes it possible to anesthetize a broader area with a lesser amount of narcotic. The proximal end of inner tube 200 protrudes sideways from a cylindrical wall of external tube 100, so that medicine inlets 500 and 600 are connected to the proximal ends of outer and inner tubes 100 and 200, respectively. The double-tube structure of the catheter, however, does not allow a piercing needle to be taken out of a patient's body and removed from the catheter while the catheter is in its operative position.

Recently, catheters of a certain double-lumen type have also been used. This type of catheter has two delivery outlets, however, appropriate connectors have not yet been proposed for attachment of external devices to the catheter's proximal end after removing the piercing needle. The diameter of each lumen in this type of catheter is so small that thin and needle-shaped connecting members must be fitted in proximal openings of the lumens and connected to external devices. This construction is disadvantageous in that liquid medicine is likely to leak out from the boundary between the catheter tube and the needle-shaped members, and the latter often cause the proximal end of the tube to be damaged or broken.

SUMMARY OF THE INVENTION

In view of the drawbacks associated with prior art catheters, an object of the present invention is to provide an epidural catheter including an adapter and a catheter body having two or more lumens extending therethrough, wherein two or more external devices for supply of a liquid medicine can easily and readily be connected through the adapter to the catheter body.

This object will be achieved herein by providing an epidural catheter that includes a catheter body having a distal end and a proximal end and having formed therein a main lumen and at least one auxiliary lumen. The main lumen and the auxiliary lumen extend side by side and in parallel with each other. The main lumen has an outlet opening at the distal end and an inlet opening at the proximal end. The auxiliary lumen has an outlet opening located behind and spaced a predetermined distance from the outlet opening in the main lumen and an inlet lateral opening located toward the proximal end.

An adapter is disposed on the catheter body. The adapter includes a forward member, a middle member and a rearward member that are detachably connected to one another. The forward, middle and rearward members each have axial bores to tightly receive the catheter body. Preferably, the axial bores in each member are coaxially aligned and have substantially the same diameter. The rearward member has a first inlet port formed therein and communicating with the inlet opening of the main lumen. The middle member has a second inlet port formed therein and communicating with the inlet opening of the auxiliary lumen. Seals are disposed between the forward and middle members and between the middle and rearward members.

The adapter may be made of a transparent thermoplastic resin so that the inlet opening of the auxiliary lumen can be seen through the adapter, when the latter is being attached to the catheter body.

The catheter body may be provided with an alignment marking so that the inlet opening of the auxiliary lumen can be readily aligned with the second inlet port formed in the middle member.

The middle and rearward members of the adapter may be formed integral with each other. Similarly, the forward and middle members may be so formed. In addition, the forward, middle and rearward members may be integrally formed into a one-piece adapter.

The adapter provided herein is not always disposed on the catheter body, but instead is attached thereto on demand only when necessary. Thus, practitioners or other users can easily take the piercing needle off the catheter body, after having introduced the catheter body into a patient's body through the needle. After the needle has been removed, the adapter connected to the catheter body will form flow paths through the adapter and catheter body, so as to enable the dosing of a narcotic or other liquid medicine. The seal disposed in the contact region between the catheter body and the adapter prevents the narcotic from leaking out of the contact region.

DETAILED DESCRIPTION OF THE PREFERRED EMBODIMENTS

An epidural catheter provided herein is composed of a catheter body and an adapter connectable thereto. An example in which the catheter body has two lumens formed therein and therealong will now be described in detail.

Figure 1:
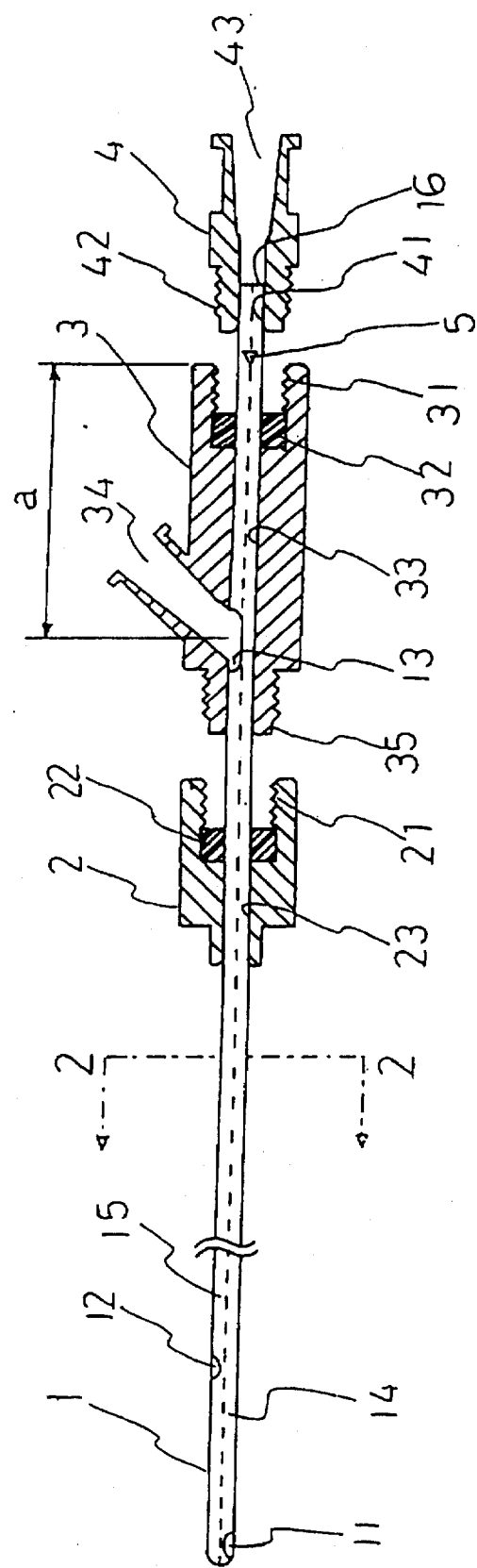
FIG. 1 is a cross-section of an epidural catheter provided in a first embodiment of the present invention.
Figure 2:
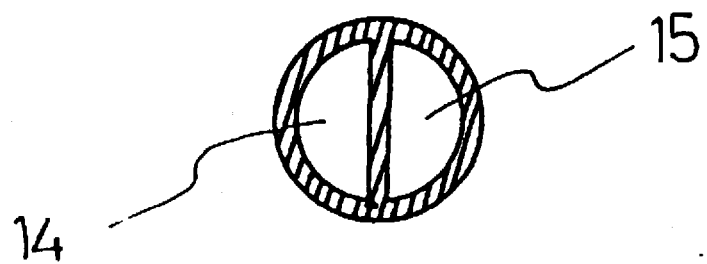
FIG. 2 is a cross-section taken along the line 2—2 in FIG. 1.

As shown in FIG. 1, the catheter body 1 includes a main lumen 14 and an auxiliary lumen 15, and the main lumen 14 has an outlet opening 11 located at a distal end of body 1. The auxiliary lumen 15 has an outlet opening 12 located behind and spaced from the distal end and a distance of 5–10 cm. An inlet opening 16 of the main lumen 14 is disposed at a proximal end of the catheter body 1, with an inlet lateral opening 13 of the auxiliary lumen 15 being disposed near and ahead of the proximal end.

The adapter includes three members 2, 3 and 4 connectable one to another. Members 2, 3 and 4 are provided with axial bores 23, 33 and 41, respectively. As shown in FIG. 1, axial bores 23, 33 and 41 are coaxially aligned and have substantially the same diameter. The forward and middle members 2 and 3, respectively, are threaded to engage with one another, with the middle and rearward members 3 and 4, respectively, also being threaded in the same manner. In detail, a male-threaded lug 35 of the middle member 3 can be fastened into a female-threaded axial cavity 21 formed in the forward member 2. Likewise, a male-threaded lug 42 of the rearward member 4 can be fastened into a female-threaded axial cavity 31 formed in the middle member 3.

Figure 3:
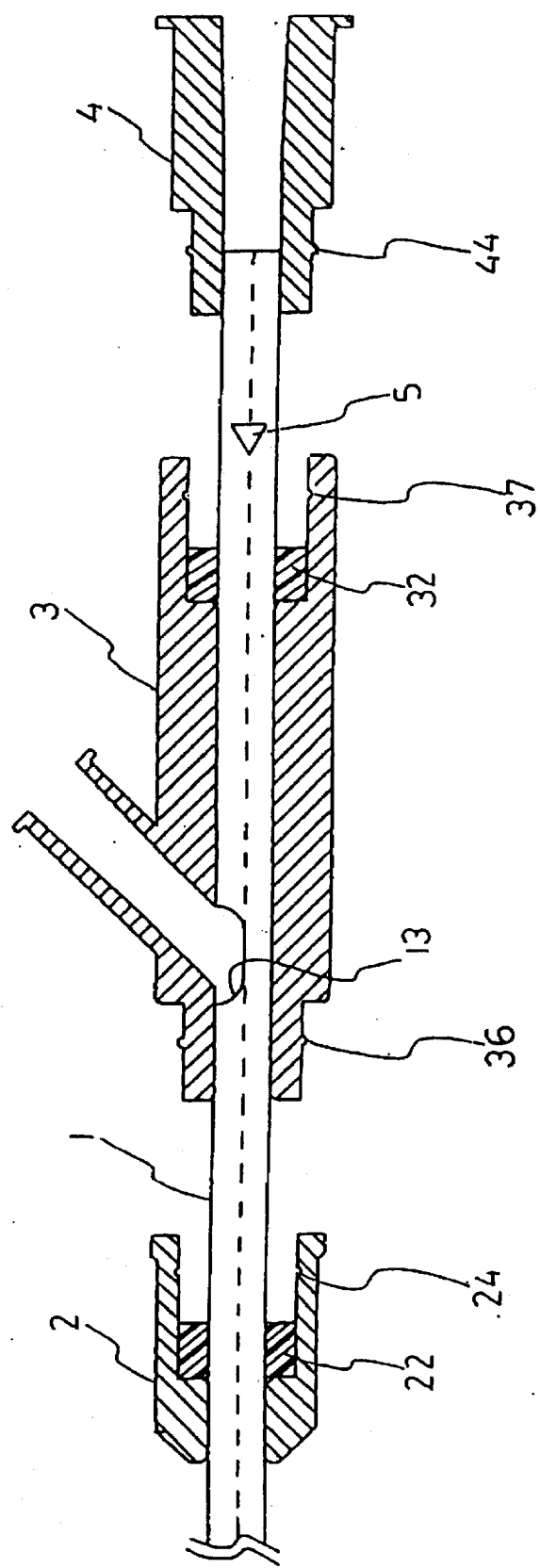
FIG. 3 is a cross-section of an epidural catheter provided in a second embodiment of the present invention.
Figure 4:
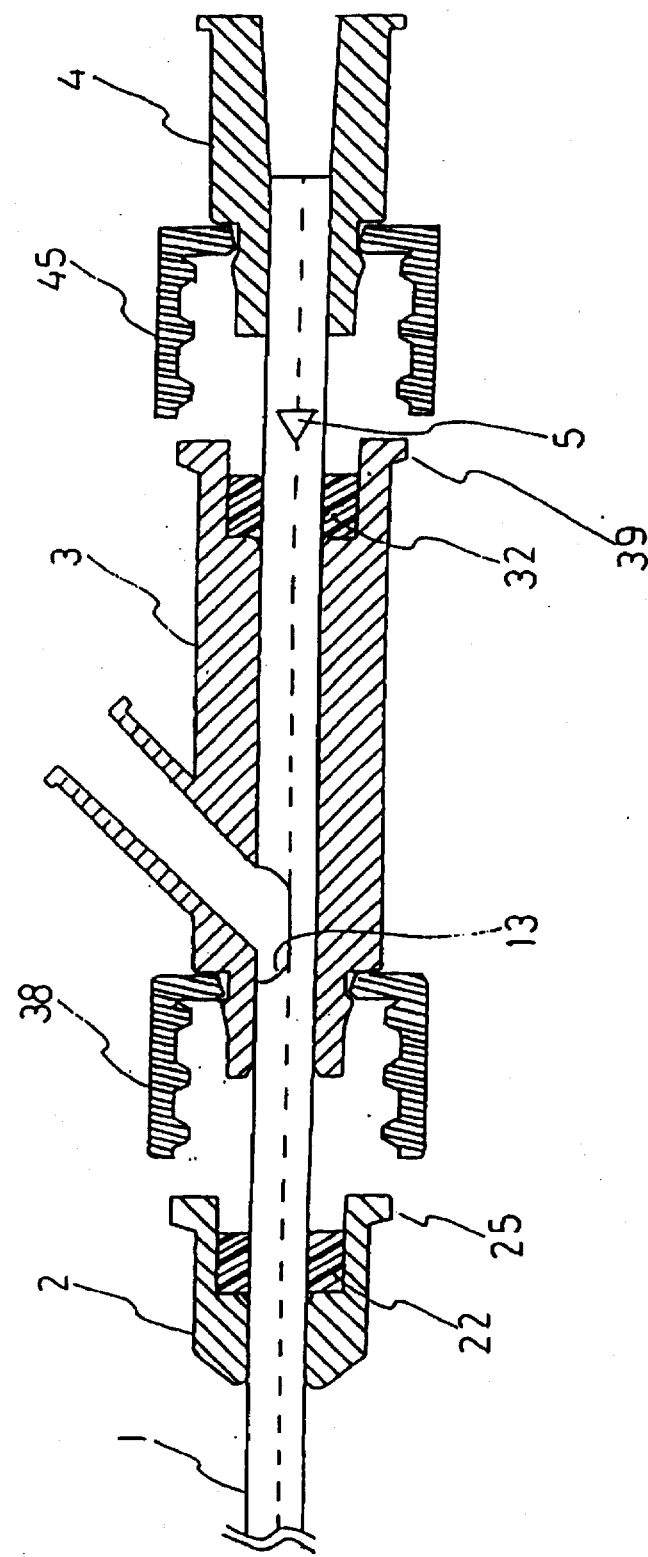
FIG. 4 is a cross-section of an epidural catheter provided in a third embodiment of the present invention.

Those skilled in the art will recognize that members 2, 3 and 4 constituting the adapter may be connected to one another in manners other than the manner shown in FIG. 1. For example, the forward and rearward members 2 and 4 may have a rearward threaded lug and a forward threaded cavity, respectively, with the middle member 3 having a cavity and a lug of complementary shapes. Alternatively, members 2, 3 and 4 may be interference-fitted on each other as shown in FIG. 3 or Luer-connected to each other as shown in FIG. 4.

Annular seals 22 and 32 are compressed by and between adjacent members 2 and 3 and adjacent members 3 and 4, respectively, of the adapter. The compressed seals have their inner peripheries reduced so as to be in forced tight contact with the outer periphery of the catheter body 1. Each seal may be disposed at a location different from the location shown in FIG. 1, as long as the seal is compressed properly. For example, the seal 22 may be attached to the front end face of the middle member's threaded lug 35.

A first inlet port 43 for receiving a liquid medicine is formed in the rearward member 4 so as to communicate with the interior of the main lumen 14. A second inlet port 34 is formed in the middle member 3 so as to communicate with the interior of the auxiliary lumen 15. The first and second inlet ports have Luer-tapered inner peripheries, so that Luer-tapered ends of, for example, syringes can closely fit in such ports.

If desired, an alignment marking may be printed on the catheter body, at a point near the proximal end thereof. Such alignment marking is helpful when aligning the second inlet port 34 with the inlet lateral opening 13 of the auxiliary lumen. In the embodiment shown in FIG. 1, marking 5 is located behind the inlet lateral opening 13 and spaced therefrom a distance "a." This distance "a" corresponds to the distance between the bottom center of second inlet port 34 and the proximal end of the middle member 3. The marking 5 may be printed in any suitable manner and its location may be varied so long as it is clearly and easily visible to the users.

The adapter as described above may be formed of a suitable thermoplastic resin such as a polycarbonate, a polystyrene or an ABS (acrylonitrile-butadiene-styrene) resin. For easy visual inspection of the alignment of the lateral inlet opening 13 with the second inlet port 34, it is preferred that the resin is transparent.

The seals incorporated in the adapter may be formed of a rubber or elastomer, such as natural rubber, butadiene rubber, styrene-butadiene rubber, isoprene, ethylene-propylene rubber, butyl rubber, chloroprene, nitrile rubber, acrylic, urethane or silicone rubber.

The catheter body may be formed of a flexible thermoplastic resin such as a polyethylene resin, a polypropylene, an ethylene-propylene copolymer, an ethylene-vinyl acetate, a polyvinyl chloride, a polyamide elastomer, a polyurethane resin or its elastomer, a composite material formed of any combination of the aforementioned materials, or an elastomer such as a silicone rubber or a latex rubber. More preferably, the catheter body is formed of a material selected from the group consisting of polyethylene, ethylene-propylene copolymer and a polyurethane elastomer.

The adapter may be attached to the catheter body 1 in the following manner. First, forward member 2 is fitted on catheter body 1 by sliding body 1 through axial bore 23 in forward member 2. Then, middle member 3 is fitted on and slid forward along catheter body 1 through axial bore 33 in the same manner, until marking 5 coincides with the proximal (rearward) end of middle member 3. After middle member 3 is threaded into forward member 2, rearward member 4 is fitted on catheter body 1 through axial bore 41 and threaded into middle member 3. The first and second inlet ports 43 and 34 of the adapter thus connected to the catheter body can then be used to dose therethrough a narcotic or other liquid medicine to a patient.

Although the catheter body 1 exemplified above is of the double-lumen type, additional lumens may be provided to form for example, a triple-lumen or quadruple-lumen catheter body in which case the adapter may include two or three middle members which intervene between the forward and rearward members.

The forward, middle and rearward members 2, 3 and 4 in the embodiment shown in FIG. 1 are separable from each other. In the 5 fourth embodiment illustrated in FIG. 5, the middle and rearward members 3 and 4 are separable from each other but have been connected to form one piece before being fitted on catheter body 1. Those skilled in the art will recognize that either forward and middle members 2 and 3 or middle and rearward members 3 and 4 may be formed so as to be integral with one another.

The epidural catheter provided in the alternative embodiments will now be briefly described. In the second embodiment shown in FIG. 3, forward member 2 is provided with an annular groove 24, middle member 3 is provided with an annular protrusion 36 as well as an annular groove 37, and rearward member 4 is provided with an annular protrusion 44 so that members 2, 3 and 4 can be joined by forcing them into an interference engagement with each other. This construction is advantageous because it avoids the need to rotate each member relative to the catheter body in the process of joining the members together, thereby protecting the catheter body from any torsion. Thus, members 2, 3 and 4 can be combined with the catheter body more rapidly and more surely. Seals 22 and 32 are disposed between adjacent members to prevent leakage of liquid medicine, as described above in connection with the assembly provided in the first embodiment.

In the third embodiment shown in FIG. 4, the rigid connection between the adapter members is accomplished in yet another way. Middle and rearward members 3 and 4 are provided with short cylindrical and female-threaded parts 38 and 45, respectively, which are rotatable relative to members 3 and 4. In corresponding fashion, forward and middle members 2 and 3 are provided with protrusions 25 and 39, respectively, which are Luer-shaped in cross section and firmly engageable with the respective threaded parts. Seals 22 and 32 are similar to those described in connection with the preceding embodiments. Since only the cylindrical parts are rotated when connecting the members to each other, twisting of catheter body 1 is minimized during the joining process.

Figure 5:
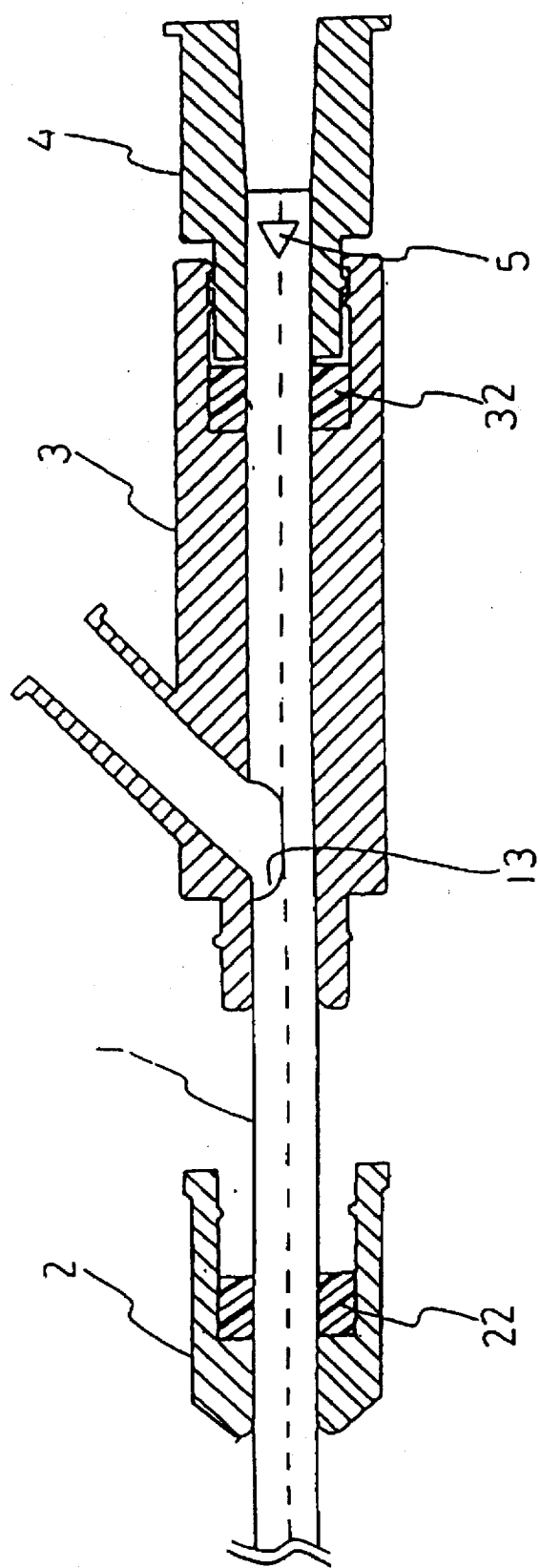
FIG. 5 is a cross-section of an epidural catheter provided in a fourth embodiment of the present invention.
Figure 6:
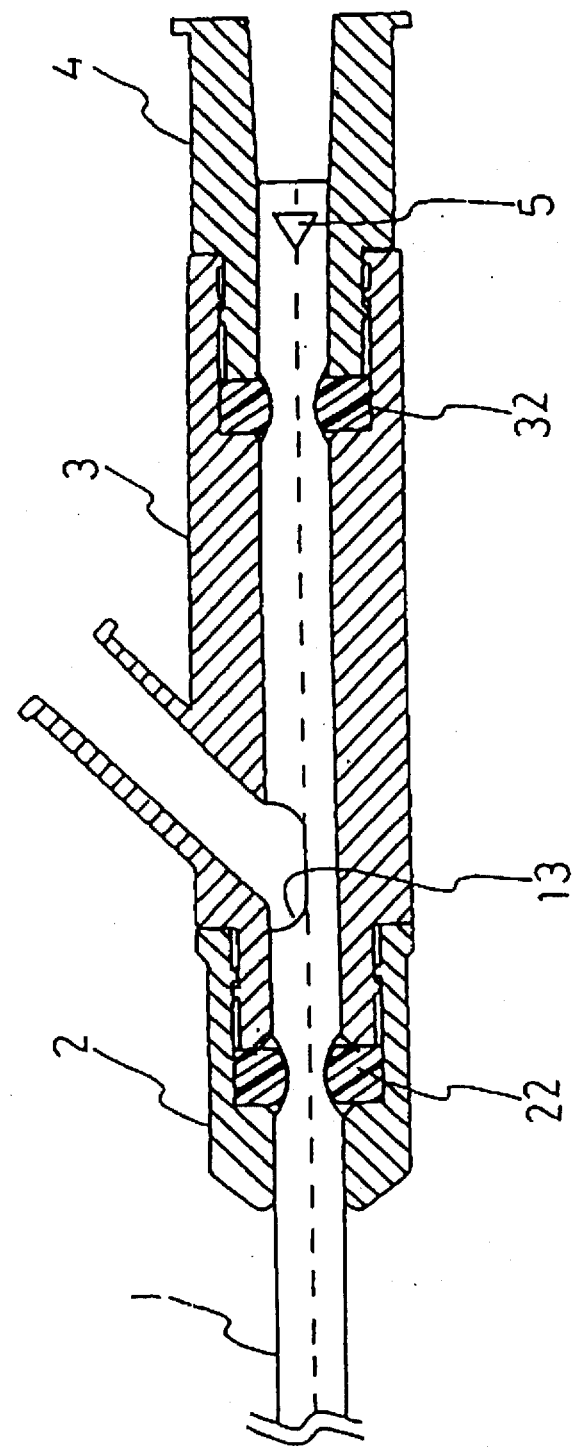
FIG. 6 is a cross-section of the epidural catheter shown in FIG. 5 in which the adapter has been secured on the catheter body.
Figure 7:
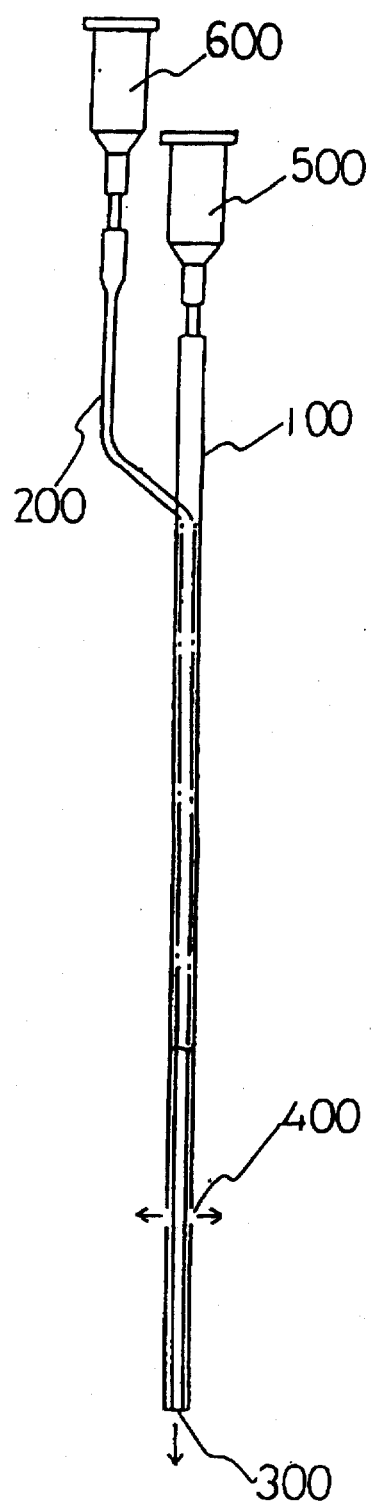
FIG. 7 shows a prior art epidural catheter of the double-tube type.

In the fourth embodiment shown in FIG. 5, middle and rearward members 3 and 4 have been connected to one another so as to become one piece before being fitted on catheter body 1. FIG. 6 shows members 3 and 4 subsequently connected to forward member 2 on catheter body 1. The adapter in this embodiment functions as if it includes two parts instead of three parts and, consequently, can be attached to body 1 more easily. Those skilled in the art will recognize that forward and middle members 2 and 3 also may be connected to one another so as to become one piece before being fitted on catheter body 1. It will also be apparent that one or more of members 2, 3 and 4 may be integrally formed with one another so as to form either a one-piece adapter or a two-piece adapter. Seals 22 and 32 are similar to those described in connection with the preceding embodiments. It will also be understood that nuts may be used to connect members 2, 3 and 4.

The apparatus described above for epidural anesthesia may be used in various manners including, for example, to dose different medicines through the lumens at different rates, or to dose medicine through one lumen and take a blood sample through the other lumen at the same time.

In summary, the multi-lumen catheter includes a catheter body and an adapter which is readily and detachably combined with the catheter body. Therefore, the piercing needle can easily be removed from a patient who is receiving epidural anesthesia, and the adapter is provided with inlet ports for the respective lumens, thus shortening the operation time. The open end of the catheter body is protected from damage such as tears or cracks and leakage of liquid from between the body and the adapter is prevented, whereby safety of medical operations using this catheter is remarkably improved.

What is claimed is:

1. An epidural catheter comprising:
    a catheter body having a distal end and a proximal end and having formed therein a main lumen and at least one auxiliary lumen, the main lumen and auxiliary lumen extending side by side and in parallel with each other, the main lumen having an outlet opening at the distal end and an inlet opening at the proximal end, the auxiliary lumen having an outlet opening spaced a predetermined distance from the outlet opening in the main lumen and an inlet lateral opening located toward the proximal end;
    an adapter detachably disposed on the catheter body, the adapter comprising forward, middle and rearward members that are detachably connected to one another, each member having an axial bore therethrough to tightly receive the catheter body, the rearward member having a first inlet port formed therein and communicating with the inlet opening of the main lumen, the middle member having a second inlet port formed therein and communicating with the inlet opening of the auxiliary lumen; and
    seals disposed between the forward and middle members and between the middle and rearward members.

2. An epidural catheter as defined in claim 1, wherein the adapter is made of a transparent thermoplastic resin so that the inlet opening of the auxiliary lumen is visible through the adapter.

3. An epidural catheter as defined in claim 2, wherein the middle and rearward members of the adapter are formed integral with each other.

4. An epidural catheter as defined in claim 3, wherein the forward and middle members are formed integral with each other.

5. An epidural catheter as defined in claim 1, wherein the catheter body is provided with an alignment marking for aligning the inlet opening of the auxiliary lumen with the second inlet port formed in the middle member.

6. An epidural catheter as defined in claim 5, wherein the middle and rearward members of the adapter are formed integral with each other.

7. An epidural catheter as defined in claim 6, wherein the forward and middle members are formed integral with each other.

8. An epidural catheter as defined in claim 1, wherein the axial bores in the forward, middle and rearward members are coaxially aligned and have substantially the same diameter.

9. An epidural catheter as defined in claim 8, wherein the middle and rearward members of the adapter are formed integral with each other.

10. An epidural catheter as defined in claim 9, wherein the forward and middle members are formed integral with each other.

11. An epidural catheter as defined in claim 1, wherein the middle and rearward members of the adapter are formed integral with each other.

12. An epidural catheter as defined in claim 11, wherein the forward and middle members are formed integral with each other.

13. An epidural catheter comprising:
a catheter body having a distal end and a proximal end and having formed therein a main lumen and an auxiliary lumen, the main lumen having an outlet opening at the distal end and an inlet opening at the proximal end, the auxiliary lumen having an outlet opening spaced a predetermined distance from the outlet opening of the main lumen and an inlet lateral opening located toward the proximal end; and adapter means for providing a first inlet port communicating with the inlet opening of the main lumen and a second inlet port communicating with the inlet opening of the auxiliary lumen.

* * * * *